United States Patent
Ellson et al.

(10) Patent No.: US 7,454,958 B2
(45) Date of Patent: Nov. 25, 2008

(54) ACOUSTIC DETERMINATION OF PROPERTIES OF RESERVOIRS AND OF FLUIDS CONTAINED THEREIN

(75) Inventors: Richard N. Ellson, Palo Alto, CA (US); Richard G. Stearns, Felton, CA (US)

(73) Assignee: Labcyte Inc., Sunnyvale, CA (US)

( * ) Notice: Subject to any disclaimer, the term of this patent is extended or adjusted under 35 U.S.C. 154(b) by 338 days.

(21) Appl. No.: 10/946,141

(22) Filed: Sep. 20, 2004

(65) Prior Publication Data

US 2005/0092058 A1 May 5, 2005

Related U.S. Application Data

(63) Continuation-in-part of application No. 10/310,638, filed on Dec. 4, 2002, now Pat. No. 6,938,995, which is a continuation-in-part of application No. 10/010,972, filed on Dec. 4, 2001, now abandoned.

(51) Int. Cl.
*G01N 29/02* (2006.01)
*G01N 29/22* (2006.01)
*G01N 29/36* (2006.01)

(52) U.S. Cl. ............ 73/61.43; 73/54.02; 73/61.49; 73/64.53; 73/64.56

(58) Field of Classification Search ............. 73/19.03, 73/32 A, 54.01, 54.02, 61.41–61.43, 61.76, 73/61.79, 64.53, 64.56
See application file for complete search history.

(56) References Cited

U.S. PATENT DOCUMENTS 3,608,715 A   9/1971  Snyder et al.
4,308,547 A   12/1981 Lovelady et al.
4,391,129 A   7/1983  Trinh et al.
4,558,589 A   12/1985 Hemmes
4,901,245 A   2/1990  Olson et al.
5,041,849 A   8/1991  Quate et al.
5,056,357 A   10/1991 Dymling et al.
5,211,054 A * 5/1993  Muramatsu et al. ........ 73/64.42
5,255,564 A   10/1993 Glad et al.

(Continued)

FOREIGN PATENT DOCUMENTS

DE   19735087 A1   3/1999

(Continued)

OTHER PUBLICATIONS

U.S. Appl. No. 09/669,194, filed Sep. 25, 2000, Ellson et al.

(Continued)

*Primary Examiner*—David A. Rogers

(57) ABSTRACT

The invention provides devices and methods for acoustically determining the properties of the contents of one or more reservoirs in a plurality of reservoirs. Each reservoir is adapted to contain a fluid. An acoustic radiation generator can be positioned in acoustic coupling relationship to each of the reservoirs. Acoustic radiation generated by the acoustic radiation generator is transmitted through each reservoir to an analyzer. The analyzer is capable of analyzing a characteristic of the transmitted acoustic radiation and optionally correlating the characteristic to a property of the reservoirs' contents. Properties that may be determined include volume, temperature, and composition. The invention is particularly suited to determining the properties of the contents of a plurality of reservoirs to allow for accuracy and control over the dispensing of fluids therefrom.

30 Claims, 6 Drawing Sheets

U.S. PATENT DOCUMENTS

| | | | |
|---|---|---|---|
| 5,263,371 A * | 11/1993 | Maresca et al. | 73/290 V |
| 5,410,518 A | 4/1995 | Birkett | |
| 5,471,872 A | 12/1995 | Cummings | |
| 5,507,178 A | 4/1996 | Dam | |
| 5,509,299 A * | 4/1996 | Sarvazjan et al. | 73/64.53 |
| 5,520,715 A | 5/1996 | Oeftering | |
| 5,533,402 A | 7/1996 | Sarvazyan et al. | |
| 5,594,165 A | 1/1997 | Madanshetty | |
| 5,623,095 A | 4/1997 | Beller | |
| 5,739,432 A | 4/1998 | Sinha | |
| 5,767,407 A | 6/1998 | Sinha | |
| 5,793,705 A | 8/1998 | Gazis et al. | |
| 5,798,779 A | 8/1998 | Nakayasu et al. | |
| 5,804,698 A | 9/1998 | Belonenko et al. | |
| 5,880,364 A | 3/1999 | Dam | |
| 5,922,945 A | 7/1999 | Allmaras et al. | |
| 5,992,223 A * | 11/1999 | Sabins et al. | 73/64.42 |
| 6,048,050 A | 4/2000 | Gundlach et al. | |
| 6,119,510 A | 9/2000 | Carasso et al. | |
| 6,196,664 B1 | 3/2001 | Kanda et al. | |
| 6,227,040 B1 | 5/2001 | Hastings et al. | |
| 6,298,726 B1 | 10/2001 | Adachi et al. | |
| 6,312,121 B1 | 11/2001 | Smith et al. | |
| 6,328,421 B1 | 12/2001 | Kojima et al. | |
| 6,336,707 B1 | 1/2002 | Asai et al. | |
| 6,364,454 B1 | 4/2002 | Hadimioglu | |
| 6,446,494 B2 * | 9/2002 | Hastings et al. | 73/54.41 |
| 6,467,877 B2 | 10/2002 | Ellson | |
| 6,596,239 B2 * | 7/2003 | Williams et al. | 422/100 |
| 6,634,233 B2 * | 10/2003 | He | 73/597 |
| 6,666,541 B2 | 12/2003 | Ellson et al. | |
| 6,912,891 B2 * | 7/2005 | Coupland et al. | 73/64.53 |
| 2001/0039830 A1 * | 11/2001 | Hastings et al. | 73/54.41 |
| 2002/0037375 A1 | 3/2002 | Ellson et al. | |
| 2002/0094582 A1 | 7/2002 | Williams et al. | |
| 2002/0155231 A1 | 10/2002 | Ellson et al. | |
| 2003/0101819 A1 * | 6/2003 | Mutz et al. | 73/602 |
| 2003/0150257 A1 * | 8/2003 | Mutz et al. | 73/61.49 |
| 2003/0172734 A1 * | 9/2003 | Greenwood | 73/597 |
| 2004/0014029 A1 | 1/2004 | Mutz et al. | |
| 2004/0191275 A1 * | 9/2004 | Milner | 424/400 |
| 2004/0226362 A1 * | 11/2004 | Marx et al. | 73/290 V |

FOREIGN PATENT DOCUMENTS

| | | |
|---|---|---|
| EP | 1208913 A2 | 5/2002 |
| EP | 1208914 A2 | 5/2002 |
| EP | 1209466 A2 | 5/2002 |

OTHER PUBLICATIONS

Amemiya et al. (1997), "Ink Jet Printing with Focsued Ultrasonic Beams," IS&T's NIP13: 1997 International Conference on Digital Printing Technologies, pp. 698-702.

* cited by examiner

ACOUSTIC DETERMINATION OF PROPERTIES OF RESERVOIRS AND OF FLUIDS CONTAINED THEREIN

CROSS-REFERENCE TO RELATED APPLICATIONS

This is a continuation-in-part of U.S. patent application Ser. No. 10/310,638, filed Dec. 4, 2002 now U.S. Pat. No. 6,938,995, which is a continuation-in-part of U.S. patent application Ser. No. 10/010,972, filed Dec. 4, 2001, abandoned. The disclosures of the aforementioned applications are incorporated herein by reference in their entireties.

TECHNICAL FIELD

The invention relates generally to the use of acoustic energy to determine a temperature-dependent property of a fluid in a reservoir and/or of the reservoir-material itself. The determined properties can be stored and optionally applied at a later time to enhance accuracy, precision, and efficiency in dispensing fluids from the reservoirs, and particularly, in dispensing fluids with the use of focused acoustic energy. Moreover, the invention provides the capability of analyzing the contents of a reservoir at any temperature, e.g., without having to thaw a frozen well plate in which each well contains a frozen fluid.

BACKGROUND

The discovery of novel and useful materials depends largely on the capacity to make and characterize new compositions of matter. As a result, recent research relating to novel materials that have useful biological, chemical, and/or physical properties has focused on the development and implementation of new methods and systems for synthesizing and evaluating potentially useful chemical compounds. In particular, high-speed combinatorial methods have been developed to address the general need in the art for systematic, efficient, and economical material synthesis techniques, as well as for methods to analyze and to screen novel materials for useful properties.

Generally, it is important to control the quality of the starting materials in any chemical synthesis process. Otherwise, the integrity of the process and the quality of the resulting product are compromised. Quality control of the starting materials is a particularly important issue in combinatorial synthesis procedures. In such procedures, a large number of starting compounds may be dispensed in a predetermined sequence from a compound library to synthesize, for example, a batch of a drug. As a further example, such procedures may be used in peptide drug discovery applications to synthesize a drug containing a specific peptide sequence. Should any of the starting compounds contain an unacceptable level of a contaminant or exhibit an unacceptable degree of degradation, the synthesized compound may be rendered useless. In effect, all starting compounds employed for the batch synthesis would be wasted. This is particularly problematic when one or more of the starting compounds are rare or expensive.

Similarly, combinatorial testing techniques may be employed in analytical and testing procedures. For example, a combination of two or more pharmacologically active candidate compounds may be delivered to a test sample in order to assess whether synergistic effects are achieved. If any one of the candidate compounds is compromised in quality, however, the accuracy and reliability of the assessment may be reduced. Thus, further testing may be necessary, adding significantly to the overall time and cost associated with the combinatorial testing process.

High-speed combinatorial methods often involve the use of array technologies that require accurate dispensing of fluids, each having a precisely known chemical composition, concentration, stoichiometry, ratio of reagents, and/or volume. Such array technologies may be employed to carry out various synthetic processes and evaluations. Array technologies may use large numbers of different fluids to form a plurality of reservoirs that, when arranged appropriately, create combinatorial libraries. In order to carry out combinatorial methods, a number of fluid dispensing techniques have been explored, such as pin spotting, pipetting, inkjet printing, and acoustic ejection. Many of these techniques possess inherent drawbacks that must be addressed, however, before the fluid dispensing accuracy required for the combinatorial methods can be achieved. For instance, a number of fluid dispensing systems are constructed using networks of tubing or other fluid-transporting vessels. Tubing, in particular, can entrap air bubbles, and nozzles may become clogged by lodged particulates. As a result, system failure may occur and cause spurious results. Furthermore, cross-contamination between the reservoirs of compound libraries may occur due to inadequate flushing of tubing and pipette tips between fluid transfer events. Cross-contamination can easily lead to inaccurate and misleading results.

Acoustic ejection provides a number of advantages over other fluid dispensing technologies. In contrast to inkjet devices, nozzleless fluid ejection devices are not subject to clogging and their associated disadvantages, e.g., misdirected fluid or improperly sized droplets. Furthermore, acoustic technology does not require the use of tubing or involve invasive mechanical actions, for example, those associated with the introduction of a pipette tip into a reservoir of fluid.

Acoustic ejection has been described in a number of patents. For example, U.S. Pat. No. 4,308,547 to Lovelady et al. describes a liquid drop emitter that utilizes acoustic principles to eject droplets from a body of liquid onto a moving document to result in the formation of characters or barcodes thereon. A nozzleless inkjet printing apparatus is used such that controlled drops of ink are propelled by an acoustical force produced by a curved transducer at or below the surface of the ink. Similarly, U.S. Pat. No. 6,666,541 to Ellson et al. describes a device for acoustically ejecting a plurality of fluid droplets toward discrete sites on a substrate surface for deposition thereon. The device includes an acoustic radiation generator that may be used to eject fluid droplets from a reservoir, as well as to produce a detection acoustic wave that is transmitted to the fluid surface of the reservoir to become a reflected acoustic wave. Characteristics of the reflected acoustic radiation may then be analyzed in order to assess the spatial relationship between the acoustic radiation generator and the fluid surface. Thus, acoustic ejection may provide an added advantage in that the proper use of acoustic radiation provides feedback relating to the process of acoustic ejection itself.

Regardless of the dispensing technique used, however, inventory and materials handling limitations generally dictate the capacity of combinatorial methods to synthesize and analyze increasing numbers of sample materials. For instance, during the formatting and dispensing processes, microplates that contain a plurality of fluids in individual wells may be thawed, and the contents of selected wells can then be extracted for use in a combinatorial method. When a pipetting system is employed during extraction, a minimum loading volume may be required for the system to function properly.

Similarly, other fluid dispensing systems may also require a certain minimum reservoir volume to function properly. Thus, for any fluid dispensing system, it is important to monitor the reservoir contents to ensure that at least a minimum amount of fluid is provided. Such content monitoring generally serves to indicate the overall performance of a fluid dispensing system, as well as to maintain the integrity of the combinatorial methods.

During combinatorial synthesis or analysis processes, environmental effects may play a role in altering the contents of reservoirs on a well plate or microplate. For example, dimethylsulfoxide (DMSO) is an organic solvent commonly employed to dissolve or suspend many of the compounds found in drug libraries. DMSO is highly hygroscopic and tends to absorb ambient water with which it comes into contact. In turn, the absorption of water dilutes the concentration the compounds as well as alters the ability of the DMSO to dissolve or suspend the compounds. Furthermore, the absorption of water may promote the decomposition of water-sensitive compounds.

Acoustic monitoring makes it possible to determine the DMSO content of DMSO/water mixtures in microplate reservoirs, for DMSO concentrations ranging from about 70 to 100% by volume. When the fluid in the microplate well is a binary mixture of DMSO and water, adding water to or removing water from the mixture results in a change in the echo amplitude from the fluid/well-bottom interface. Measurement of the amplitude of reflection from microplate surfaces enables a calculation of acoustic impedance for the liquid in the microplate well. When acoustic impedance is translated to DMSO concentration in a DMSO/water mixture by the appropriate empirical model, the results are accurate to within a few percentage points at room temperature.

However, if the microplate temperature deviates from room temperature, both the acoustic impedance of the microplate, and potentially that of the fluid in the wells, will change. As a consequence, the change in the amplitude of reflection for acoustic energy at the fluid/well interface will be interpreted as a change in DMSO/water composition.

For example, if a microplate containing a frozen DMSO/water mixture is processed by an acoustic instrument, e.g., the Echo 550 instrument (Labcyte Inc., Sunnyvale, Calif.), the initial DMSO content is incorrectly measured as being less than 40%. It takes nearly one hour before the microplate warms to room temperature, when the equilibrium acoustic impedances needed for the room temperature empirical model described above are reached, so that the composition of the DMSO/water mixtures in the wells can be accurately measured.

Benefits in accuracy and in time used would be obtained if microplates did not have to be at thermal equilibrium in order to accurately measure fluid composition in a well. A device and method is needed for making accurate compositional measurements without having to bring well plates to room temperature, by compensating for thermal variations in acoustic impedance and changes in the resulting echoes.

A number of patents describe the use of acoustic energy to assess the contents of a container. U.S. Pat. No. 5,507,178 to Dam, for example, describes a sensor for determining the presence of a liquid and for identifying the type of liquid in a container. The ultrasonic sensor determines the presence of the liquid through an ultrasonic liquid presence sensing means and identifies the type of liquid through a liquid type identification means, and includes a pair of electrodes and an electrical pulse generating means. This device suffers from the disadvantage that the sensor must be placed in contact with the liquid.

U.S. Pat. No. 5,880,364 to Dam, on the other hand, describes a non-contact ultrasonic system for measuring the volume of liquid in a plurality of containers. An ultrasonic sensor is disposed opposite to the tops of the containers. A narrow beam of ultrasonic radiation is transmitted from the sensor to the open top of an opposing container, and is then reflected from the air-liquid interface of the container back to the sensor. By using the round trip transit time of the radiation and the dimensions of the containers being measured, the volume of liquid in the container can be calculated. This device cannot be used to assess the contents of sealed containers. In addition, the device lacks precision because air is a poor conductor of acoustic energy. Thus, while this device may provide rough estimates of the volumes of liquid in relatively large containers, it is unsuitable for use in providing a detailed assessment of the contents of reservoirs typically used in combinatorial techniques. In particular, this device cannot determine the position of the bottom of containers, since substantially all of the emitted acoustic energy is reflected from the liquid surface and does not penetrate to detect the bottom. Low volume reservoirs in microplates are regular arrays of fluid containers, and the location of the bottoms of the containers can vary by a significant fraction of the nominal height of a container due to distortions in the plate, such as bowing. Thus, detection of only the position of the liquid surface leads to significant errors in height and thus volume estimation in common containers.

There is thus a need in the art for improved methods and devices that are capable of determining temperature-dependent properties of reservoirs and fluids contained therein. Such capabilities would be particularly useful for tracking the quality of compound libraries in solution, and the quantities of the compounds therein, for combinatorial and screening applications. In particular, it would be useful to determine such properties for a range of reservoir and microplate temperatures.

SUMMARY OF THE INVENTION

In one embodiment, the invention provides a method for acoustically determining a temperature-dependent property of a fluid in a reservoir, the reservoir being integral with or located on a substrate. The method comprises the following steps:

(a) acoustically coupling an acoustic radiation generator and the reservoir, with the acoustic radiation generator located external to the reservoir;

(b) activating the acoustic radiation generator to generate acoustic radiation and direct the acoustic radiation generated into and through the substrate toward the reservoir, such that the acoustic radiation is transmitted into the fluid in the reservoir and thereafter reflected from an interior surface of the reservoir;

(c) measuring a temperature-dependent characteristic of the reflected acoustic radiation, said characteristic selected so as to correlate with a temperature-dependent property of the fluid; and (d) analyzing the characteristic to determine the temperature-dependent property of the fluid.

In a preferred embodiment of the present invention, the property of the fluid to be analyzed is fluid composition, e.g., the ratio of one fluid to another in any given reservoir. An example of such an analysis involves determining the ratio of DMSO to water in a mixture of the two solvents, as DMSO/water mixtures are often used to dissolve or suspend compounds commonly found in drug libraries.

Typically, well plates and microplates that contain a plurality of reservoirs are stored prior to use under refrigerated conditions, to chill or freeze the fluids in the reservoirs prior to use. In the method of the present invention, it is possible to provide information to the analyzer to determine the temperature of frozen fluids in a well plate and thereby to process acoustic radiation reflected at a frozen fluid/reservoir interface to determine the composition of such frozen fluid. The method may also be used to measure the temperature of the well plate.

In another embodiment, then, a method is provided for acoustically determining a temperature-dependent property of a reservoir material, the method comprising:

(a) acoustically coupling an acoustic radiation generator and the reservoir, with the acoustic radiation generator located external to the reservoir;

(b) activating the acoustic radiation generator to generate acoustic radiation and direct the acoustic radiation generated through an exterior surface of the reservoir toward an interior surface of the reservoir such that acoustic radiation is thereafter reflected from an interior surface of the reservoir;

(c) measuring a temperature-dependent characteristic of the reflected acoustic radiation, said characteristic selected so as to correlate with a temperature-dependent property of the reservoir material; and (d) analyzing the characteristic to determine the temperature-dependent property of the reservoir material.

In still another embodiment, the invention relates to a method for acoustically determining a property of a fluid disposed in a reservoir or, optionally, in each of a plurality of fluid reservoirs. The method involves selecting a reservoir from the plurality of reservoirs, each comprising a solid surface disposed on a substrate, wherein a portion of each reservoir is adapted to contain a fluid, and positioning an acoustic radiation generator in an acoustically coupled relationship to the selected reservoir. Once positioned, the acoustic radiation generator is actuated so that generated acoustic radiation is transmitted through the selected reservoir to be reflected from an interface between the fluid and the reservoir to an analyzer for processing. Even if the well is empty or the measurement is made from a sidewall rather than from the bottom, acoustic radiation directed through the chosen site will be reflected from the air/site or fluid/site interface to the analyzer. The analyzer then processes the reflected radiation to determine a characteristic thereof, which provides information about a property of the fluid in the selected reservoir. Optionally, the acoustic radiation generator can be repositioned to provide information about a property of the fluid in the remaining reservoirs.

Typically, a property of the fluid in the selected reservoir is determined by processing the acoustic radiation transmitted through the reservoir. The results of the acoustic analysis may be stored electronically for later use.

Typically, the inventive device includes a single acoustic radiation generator and a plurality of removable reservoirs. However, the inventive device can comprise a plurality of acoustic generators, such as those described in U.S. patent application Ser. No. 10/310,638 to Mutz et al., which each span more than one well. In addition, the acoustic radiation generator may comprise a component common to the analyzer, such as a piezoelectric element. Optionally, the acoustic generator may represent a component of an acoustic ejector, which ejects droplets from the reservoirs. In such a case, the device may further comprise a means to focus the acoustic radiation.

In a further embodiment, the invention provides a device for acoustically determining a property of a fluid in a reservoir adapted to contain the fluid, the reservoir being contained in or disposed on a solid surface of a substrate. The device includes an acoustic radiation generator for generating acoustic radiation. The device also includes means for positioning the acoustic radiation generator in an acoustically coupled relationship to the reservoir. The acoustic radiation generator is then actuated to transmit acoustic radiation through the reservoir, to be reflected from an interface between the fluid and the reservoir. The acoustic radiation reflected from the interface is delivered to an analyzer for processing. The analyzer then processes the reflected acoustic radiation to determine a characteristic thereof that provides information about a property of the fluid in the reservoir. Even if the reservoir is empty, the reflected acoustic energy from the air/reservoir interface can still be used to compute the temperature of the well plate material at the reservoir.

Reflections from other interfaces in the well plate can be subjected to a similar analysis, e.g., the reflection from the bottom of the microplate and from the top of the microplate wall in between wells. Transit times for such reflections can be used, for example, to determine temperatures.

BRIEF DESCRIPTION OF THE DRAWINGS

FIG. 1A shows the acoustic ejector acoustically coupled to the first reservoir; the ejector is activated in order to eject a droplet of fluid from within the first reservoir toward a site on a substrate surface to form a feature of an array. FIG. 1B shows the acoustic ejector acoustically coupled to a second reservoir.

DETAILED DESCRIPTION OF THE INVENTION

Figure 1A:
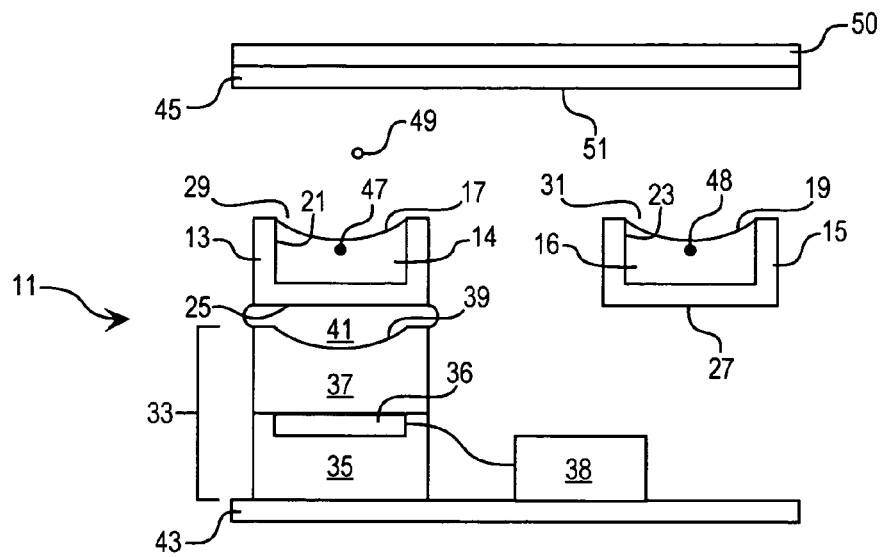
FIGS. 1A and 1B, collectively referred to as FIG. 1, schematically illustrate in simplified cross-sectional view a preferred embodiment of the inventive device. This embodiment allows both the acoustic assessment, in reflective mode, of the contents of a plurality of reservoirs, and the ejection of fluid droplets therefrom. As depicted, the device comprises first and second reservoirs, a combined acoustic analyzer and ejector, and an ejector positioning means.

Before describing the present invention in detail, it is to be understood that this invention is not limited to specific fluids, biomolecules, or device structures, as such may vary. It is also to be understood that the terminology used herein is for the purpose of describing particular embodiments only, and is not intended to be limiting.

It must be noted that, as used in this specification and the appended claims, the singular forms "a," "an," and "the" include plural referents unless the context clearly dictates otherwise. Thus, for example, reference to "a reservoir" includes a plurality of reservoirs, reference to "a fluid" includes a plurality of fluids, reference to "a biomolecule" includes a combination of biomolecules, and the like.

In describing and claiming the present invention, the following terminology will be used in accordance with the definitions set forth below.

When a first object is stated to be "acoustically coupled to" or "in an acoustic coupling relationship with" a second object, it is intended that the objects are positioned so as to allow acoustic radiation to be transferred between the objects without substantial loss of acoustic energy. When two entities are indirectly acoustically coupled, an "acoustic coupling medium" provides an intermediate medium through which acoustic radiation may be transmitted. For example, an acoustic ejector may be acoustically coupled to a fluid by immersing the ejector in the fluid or by interposing an acoustic coupling medium between the ejector and the fluid, in order to transfer acoustic radiation generated by the ejector through the acoustic coupling medium and into the fluid.

The terms "biomolecule" and "biological molecule" are used interchangeably herein to refer to any organic molecule that is, was, or can be a part of a living organism, regardless of whether the molecule is naturally occurring, recombinantly produced, or chemically synthesized in whole or in part. The terms encompass, for example, nucleotides, amino acids, and monosaccharides, as well as oligomeric, polymeric, and macromolecular species, such as oligonucleotides, polynucleotides, polypeptides, proteins, disaccharides, oligosaccharides, polysaccharides, mucopolysaccharides, peptidoglycans, and the like.

The term "fluid," as used herein to refer to the material that the "reservoirs" herein are adapted to contain, generally although not necessarily refers to matter that is at least partially nonsolid, or at least partially gaseous and/or liquid, but not entirely gaseous. A "partially nonsolid fluid" will generally be a mixture of a liquid and a solid that is minimally, partially, or fully solvated, dispersed, or suspended in the liquid. Examples of fluids include, without limitation, aqueous liquids, including water per se and salt water, and nonaqueous liquids such as organic solvents and the like. Combinations of fluids are encompassed by the term as well, and include, by way of example, compositions containing two or more miscible and/or immiscible liquids. For the purpose of the present invention, a fluid in a reservoir may be cooled to a temperature at which the fluid becomes partially or completely frozen, and will sometimes still be referred to herein as a "fluid."

The terms "focusing means" and "acoustic focusing means" refer to a means for causing acoustic waves to converge at a focal point, either by a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as are known in the art and described, for example, in U.S. Pat. No. 5,798,779 to Nakayasu et al. and Amemiya et al. (1997) Proceedings of the 1997 IS&T NIP13 International Conference on Digital Printing Technologies, pp. 698-702.

The term "moiety" refers to any composition of matter or a fragment or mixture thereof, e.g., e.g., a molecular fragment, an intact molecule (including a monomeric molecule, an oligomeric molecule, and a polymer), or a mixture of materials (for example, an alloy or a laminate).

"Optional" or "optionally" means that the subsequently described circumstance may or may not occur, so that the description includes instances where the circumstance occurs and instances where it does not.

The term "reservoir" as used herein refers to any means for containing a fluid, e.g., a receptacle or chamber. In some instances the reservoir is contained in or disposed on a solid surface of a substrate. A fluid contained in a reservoir necessarily will have a free surface, e.g., a surface that allows acoustic radiation to be reflected therefrom or a surface from which a droplet may be acoustically ejected. A reservoir may also be a locus on a substrate surface within which a fluid can be constrained. A reservoir may also be a well in a well plate.

The term "substrate" as used herein refers to any material that (1) has a surface onto which one or more fluids may be deposited, (2) contains one or more fluid reservoirs, or (3) can serve as a support for one or more fluid reservoirs permanently affixed thereto or otherwise placed thereon.

The invention accordingly relates to methods and devices for acoustically determining one or more properties of the contents of a plurality of fluid reservoirs.

The device used in conjunction with the present method generally, although not necessarily, includes a plurality of reservoirs, each adapted to contain a fluid, and an acoustic radiation generator for generating acoustic radiation. The device also includes a means for acoustically coupling the acoustic radiation generator with a reservoir and/or a fluid contained therein, such that acoustic radiation generated by the acoustic radiation generator is transmitted through at least a portion of the reservoir. An analyzer for analyzing a temperature-dependent characteristic of acoustic radiation reflected from an interior surface of the reservoirs is positioned to receive the reflected acoustic radiation.

The device may include the reservoirs as integral or permanently affixed components of the device. However, to provide for modularity and interchangeability of components, it is preferred that the reservoirs to be removable from the device. Generally, the reservoirs are arranged in a pattern or an array to provide each reservoir with individual systematic addressability. In addition, while discrete reservoirs may be provided, in circumstances that require a large number of reservoirs, it is preferred that the reservoirs are attached to each other or represent integrated portions of a single reservoir unit. For example, the reservoirs may represent individual wells in a well plate. Many well plates suitable for use with the device are commercially available and may contain, for example, 96, 384, 1536, or 3456 wells per well plate. Manufacturers of suitable well plates for use in the employed device include Corning, Inc. (Corning, N.Y.) and Greiner America, Inc. (Lake Mary, Fla.). However, the availability of such commercially available well plates does not preclude the manufacture and use of custom-made well plates containing at least about 10,000 wells, or as many as 100,000 to 500,000 wells, or more.

Furthermore, the material used in the construction of reservoirs must be compatible with the fluids contained therein. Thus, if it is intended that the reservoirs contain an organic solvent such as acetonitrile, polymers that dissolve or swell in acetonitrile would be unsuitable for use in forming the reservoirs or well plates. Similarly, reservoirs or wells intended to contain DMSO must be compatible with DMSO. For water-based fluids, a number of materials are suitable for the construction of reservoirs and include, but are not limited to, ceramics such as silicon oxide and aluminum oxide, metals such as stainless steel and platinum, and polymers such as polyester and polytetrafluoroethylene. For fluids that are photosensitive, the reservoirs may be constructed from an optically opaque material that has sufficient acoustic transparency for substantially unimpaired functioning of the device.

Generally, a single acoustic radiation generator is used, though a plurality of acoustic radiation generators may be used. All acoustic radiation generators employ a vibrational element or transducer to generate acoustic radiation. Commonly, a piezoelectric element is employed to convert electrical energy into mechanical energy associated with acoustic radiation. When a single acoustic radiation generator is used, the positioning means should allow for the acoustic radiation generator to move from one reservoir to another quickly and in a controlled manner, thereby allowing fast and controlled scanning of the contents of the reservoirs.

In some instances, the analyzer is positioned in fixed alignment with respect to the acoustic radiation generator. In other instances, however, a means similar to that described above is provided for altering the relative position of the analyzer with respect to the reservoirs. The relative position of the analyzer and the acoustic radiation generator depends on the particular configuration of the device. In some instances, the device may be configured to operate in transmissive mode, such that the generated radiation is transmitted through the entirety of the reservoir undergoing analysis. In such a case, the reservoir may be interposed between the acoustic radiation generator and an acoustic analyzer. As another option, the device may be configured to operate in a reflective mode, such that the acoustic radiation is transmitted only through a portion the reservoir whose contents are being assessed. In such a case, the analyzer may be positioned in a manner appropriate for this configuration, e.g., in order to receive reflected acoustic radiation. In any case, the acoustic radiation generator should be positioned such that generated acoustic radiation is transmitted through the portion of each reservoir most likely to contain a fluid, for optimal performance. This reduces the chance that the analyzer will erroneously determine that a reservoir is empty. For example, as fluids ordinarily flow to the bottom of containers or are driven there by centrifugation, the acoustic radiation generator should be positioned such that generated acoustic radiation is transmitted through the bottom of a reservoir.

In a preferred configuration, as discussed in detail below, the analyzer is positioned to receive acoustic radiation reflected from a free surface of a fluid contained in each reservoir. In such a configuration, the acoustic radiation generator may comprise a component common to the analyzer. The component common to the acoustic radiation generator and the analyzer may be a vibrational element that converts one form of energy into another, e.g., a piezoelectric element that converts acoustic/mechanical energy to electrical energy.

As discussed above, the reservoirs may be constructed to reduce the amount of movement and time needed to align the acoustic radiation generator with each reservoir or reservoir well during operation. As a general matter of convenience and efficiency, it is desirable to analyze an entire library of different moieties in a relatively short amount of time, e.g., about one minute. Thus, the method typically allows for the analysis of a fluid in the reservoirs at a rate of at least about 96 reservoirs per minute. Faster analysis rates of at least about 384, 1536, and 3456 reservoirs per minute are achievable with present day technology as well. Thus, the method can be implemented to analyze the properties of the fluid contents of each well of most (if not all) well plates that are currently commercially available. Proper implementation of the inventive method should yield a reservoir analysis rate of at least about 10,000 reservoirs per minute. Current commercially available positioning technology allows the acoustic radiation generator to be moved from one reservoir to another, with repeatable and controlled acoustic coupling at each reservoir, in less than about 0.1 second for high performance positioning means and in less than about 1 second for ordinary positioning means. A custom designed system will allow the acoustic radiation generator to be moved from one reservoir to another with repeatable and controlled acoustic coupling in less than about 0.001 second.

In addition, to reduce the amount of movement and time needed to align the acoustic radiation generator with each reservoir or reservoir well during operation, as discussed infra, it is preferable in some instances that the center of each reservoir be located not more than about 1 centimeter, preferably not more than about 1 millimeter, and optimally not more than about 0.5 millimeter, from a neighboring reservoir center. These dimensions tend to limit the size of the reservoirs to a maximum volume. The reservoirs are constructed to contain typically no more than about 1 mL, preferably no more than about 1 µL, and optimally no more than about 1 nL, of fluid. To facilitate handling of multiple reservoirs, it is also preferred that the reservoirs be substantially acoustically indistinguishable. In other embodiments, when working with small fluid volumes is unnecessary, the reservoirs may have a volume of 1 mL or greater, although reservoir volume will generally tend to be less than 500 µL.

By analyzing acoustic radiation that has been transmitted through at least a portion of a selected reservoir, one may accurately determine a temperature-dependent property of a fluid contained in a reservoir and/or of the reservoir material itself. As discussed above, fluid properties that may be determined include, but are not limited to, viscosity, surface tension, temperature, acoustic impedance, solid content, and impurity content. In some instances, the assessment may involve measuring the travel time of acoustic radiation through the reservoir. For example, the transit time for sound through a well plate bottom can be used as a thermometer for the microplate at a given well location.

For most materials, the speed of sound changes with temperature. By sampling sound reflected from the microplate material interfaces at a high enough rate, the change in the transit time due to the temperature dependence of the speed of sound can be detected. For example sampling at a rate that is in excess of 100 times the transit time could detect a 1% change in the speed of sound. Higher sampling rates would allow for more sensitive measurements and for the use of thinner materials.

Polypropylene is a material commonly used to make the microplates employed in compound library storage. The travel time through a polypropylene microplate bottom increases as it warms, due to the reduction in the speed of sound with temperature typical for a polypropylene material. For example, Profax™ Polypropylene shows a 0.342% reduction in the speed of sound per ° C. at temperatures near room temperature (approximately 22° C.). If a Profax Polypropylene plate experienced a 10% reduction in the speed of sound as it warmed to room temperature, an approximate 30° C. warming of the microplate bottom would be indicated.

If the transit time is known for a plate that is made of a material for which the speed of sound is a known function of temperature, the plate can act as a thermometer. This transit time would give a "bulk temperature" based on the average velocity of sound through the well bottom. If the "bulk temperature" were indicative of the fluid/plate interface temperature, then accurate values of impedance for the materials can be used to determine the reflected echo amplitude. From such data, a temperature-corrected/compensated impedance model and a reflection amplitude curve can be constructed or empirically derived.

The reflected wave at an interface depends on the acoustic impedances (Z) of the two materials forming the interface, e.g., Zfld of the fluid and Zwp of the well plate. Because both Zfld and Zwp change with temperature, the magnitude of the reflected wave used to determine the fluid composition also changes with temperature. Knowledge of the temperature of already characterized materials at the interface provides impedance information for the microplate, and enables the proper interpretation of the reflected amplitude as a function of the impedance of the fluid. The impedance information combined with temperature information provides an accurate measure of fluid composition. Accurate information about the fluid cannot be obtained without knowledge of the temperature of the materials and of the impedance of the microplate material. Determining the material composition of fluids within reservoirs, e.g., wells in microplates, involves an analysis of the reflection of acoustic energy from interfaces such as that between the fluid and the bottom, interior surface of the reservoir. The amount of reflected acoustic energy, R, from the interface and the transmitted energy, T, across the interface can be calculated from the acoustic impedance, Z, of the interface materials. For a microplate plastic with acoustic impedance of $Z_p$ and a well fluid with acoustic impedance of $Z_f$ the reflected and transmitted acoustic energy is given by Equations (1a) and (1b):

$$R = \left(\frac{Z_p - Z_f}{Z_p + Z_f}\right)^2 \quad (1a)$$

$$T = \frac{4Z_p Z_f}{(Z_p + Z_r)^2} \quad (1b)$$

The acoustic impedance changes with temperature for both the microplate and the well fluid (or solid at temperatures below the freezing point of the fluid) can be utilized over a broad temperature range (minus 80° C. up to a "warm" room temperature). The method of using the transit time in thermometry is a critical first step in the process of obtaining an "in situ" temperature measurement at the interface between the well and well contents for each well in a microplate, so that the proper impedances based on temperature are obtained and used.

An improvement to the above temperature measurement method is to use the reflection amplitude from the microplate bottom at room temperature to confirm that the acoustic impedance of the microplate material matches the expected value for a room temperature measurement. This surface should be at the same temperature as the liquid used to provide an acoustic path to the well.

Note that the dependence of the speed of sound, reflection amplitude, and acoustic impedance on temperature can be approximated by linear functions over a certain range of temperatures. Deviations from this linear behavior are seen in some materials used in acoustic applications, as well as in most materials over broad temperature ranges. In particular, temperature-dependent properties can exhibit anomalies at phase change boundaries, such as at the melting point of the fluid in the reservoir, when both liquid and solid material may coexist in the reservoir.

In addition, or in the alternative, the assessment of reservoir contents may involve determining the difference of acoustic radiation properties before and after transmission through the reservoir. For temperature-dependent properties, temperature measurement means known in the art, such as thermocouples, may be used in conjunction with such analyses. Or, as suggested above, for a known material and/or geometry, a temperature-dependent property such as the speed of sound or acoustic impedance can be determined from an acoustic measurement; this can be used to establish the temperature where the measurement was taken.

Optionally, the results of acoustic analysis performed by the acoustic analyzer may be stored. Thus, the inventive device may include, for example, a storage means comprising rewritable and/or permanent data storage media for storing the results of acoustic analysis performed by the analyzer.

Acoustic assessment as described above may be employed to improve fluid dispensing from each of a plurality of reservoirs adapted to contain a fluid. Thus, another embodiment of the invention relates to a device for dispensing fluid from each of a plurality of reservoirs adapted to contain a fluid. This device may include any of a number of known techniques for dispensing fluids involving contact-based fluid dispensing, e.g., pin spotting, pipetting, and inkjet printing, or non-contact based fluid dispensing, e.g., acoustic ejection. However, the device represents an improvement over the fluid dispensing devices known in the art, since it provides for enhanced accuracy, precision, and efficiency in fluid dispensing through the use of a means for acoustically determining one or more properties of the fluid within reservoirs and/or the reservoir materials themselves.

As discussed above, acoustic ejection provides a number of advantages over other fluid dispensing technologies. An additional advantage of the invention is that it provides a device that can carry out both acoustic ejection and assessment. In such a case, the acoustic radiation generator may serve as a component of both an acoustic ejector and an acoustic assessing means. For example, compatible acoustic ejection technology described in U.S. Ser. No. 09/964,212 involves an ejector comprising an acoustic radiation generator for generating acoustic radiation and a focusing means for focusing the acoustic radiation generated at a focal point within and sufficiently near the fluid surface in each of a plurality of reservoirs to result in the ejection of droplets therefrom.

Optionally, a focusing means is typically provided for focusing the acoustic radiation generated by the acoustic generator. In the present invention, any of a variety of focusing means may be employed in conjunction with the acoustic generator in order to eject droplets from a reservoir through the use of focused acoustic radiation. For example, one or more curved surfaces may be used to direct acoustic radiation to a focal point near a fluid surface. One such technique is described in U.S. Pat. No. 4,308,547 to Lovelady et al. Focusing means with a curved surface have been incorporated into the construction of commercially available acoustic transducers, such as those manufactured by Panametrics Inc. (Waltham, Mass.). In addition, Fresnel lenses are known in the art for directing acoustic energy at a predetermined focal distance from an object plane. See, e.g., U.S. Pat. No. 5,041,849 to Quate et al. Fresnel lenses may have a radial phase profile that diffracts a substantial portion of acoustic energy into a predetermined diffraction order at diffraction angles that vary radially with respect to the lens. The diffraction angles should be selected to focus the acoustic energy within the diffraction order on a desired object plane. Optimally, the device is adapted to eject fluid from a reservoir according to the results of acoustic analysis performed by the analyzer.

The device may also provide certain performance-enhancing functionalities. For example, the device may include a means for controlling the temperature of one or more of the reservoirs. Such temperature controlling means may be employed in the inventive device to improve the accuracy of measurement, and may be employed regardless of whether the device includes a fluid dispensing functionality. In the case of aqueous fluids, the temperature controlling means should have the capacity to maintain the reservoirs at a temperature above about 0° C. In addition, the temperature controlling means may be adapted to lower the temperature in the reservoirs. Such temperature lowering may be required because repeated application of acoustic energy to a reservoir of fluid may result in heating of the fluid. Such heating can result in unwanted changes in fluid properties, such as viscosity, surface tension, and density. Design and construction of such temperature controlling means are known to one of ordinary skill in the art and may comprise, e.g., components such as a heating element, a cooling element, or a combination thereof. For many biomolecular applications, reservoirs of fluids are stored frozen and thawed for use. During use, it is generally desired that the fluid containing the biomolecule be kept at a constant temperature, with deviations of no more than about 1 or 2° C. therefrom. In addition, for a biomolecular fluid that is particularly heat sensitive, it is preferred that the fluid be kept at a temperature that does not exceed about 10° C. above the melting point of the fluid, preferably at a temperature that does not exceed about 5° C. above the melting point of the fluid. Thus, for example, when the biomolecule-containing fluid is aqueous, it may be optimal to keep the fluid at about 4° C. during ejection. It is desirable to measure the temperature in the fluid, or to infer this temperature from the measured temperature of the reservoir containing it, to provide input to a thermal controller and to use in the determination of acoustic parameters that may be temperature dependent.

Moreover, the device may be adapted to assess and/or dispense fluids of virtually any type and amount desired. The fluid may be aqueous and/or non-aqueous. Examples of fluids include, but are not limited to, aqueous fluids including water per se and water-solvated ionic and non-ionic solutions, organic solvents, lipid liquids, mixtures of immiscible fluids, and suspensions or slurries of solids in liquids. Because the invention is readily adapted for use with high temperatures, fluids such as liquid metals, ceramic materials, and glasses may be used; see, e.g., U.S. Pat. No. 6,548,308 to Ellson and Mutz for "Method and Apparatus for Generating Droplets of Immiscible Fluids." Furthermore, because of the precision that is possible using the inventive technology, the device may be used to eject droplets from a reservoir adapted to contain no more than about 100 nanoliters of fluid, preferably no more than 10 nanoliters of fluid. In certain cases, the ejector may be adapted to eject a droplet from a reservoir adapted to contain about 1 to about 100 nanoliters of fluid. This is particularly useful when the fluid to be ejected contains rare or expensive substances, wherein it may be desirable to eject droplets having a volume of about 1 picoliter (pL) or less, e.g., having a volume in the range of about 0.025 pL to about 1 pL.

Thus, another embodiment of the invention relates to a method for dispensing fluid from one or more reservoirs. Once an acoustic radiation generator is positioned in acoustic coupling relation to a reservoir selected from a plurality of reservoirs, acoustic radiation generated by the acoustic radiation generator may be transmitted through at least a portion of the selected reservoir. The acoustic radiation is then analyzed in order to determine the properties of the contents of the reservoir, and fluid is dispensed from the selected reservoir according to that determination. Typically, the fluid is dispensed through acoustic ejection, though the inventive method may employ contact-based fluid dispensing, either as an alternative to or as a supplement to non-contact fluid dispensing. Optionally, the above process may be repeated for additional reservoirs.

It should be noted that there are a number of different ways to combine acoustic evaluation of fluid properties with fluid dispensing, depending on the intended purpose of the combination. As discussed above, fluid may be dispensed from a reservoir after the properties of the fluid in the reservoir have been acoustically determined. This allows an operator to fine-tune the dispensing according to the properties of the contents of the reservoir. In addition, fluid may be dispensed from a reservoir before the properties of the contents of the reservoir are acoustically assessed. In such a case, acoustic evaluation may serve to confirm the quality of fluid dispensation as well as to ensure that the dispensing process does not unexpectedly alter the contents of the reservoir. In some instances, acoustic assessment and fluid dispensation may occur simultaneously.

FIG. 1 illustrates a preferred embodiment of the inventive device in simplified cross-sectional view. In this embodiment, the inventive device allows for acoustic assessment of the contents of a plurality of reservoirs as well as acoustic ejection of fluid droplets from the reservoirs. The inventive device is shown in operation to form a biomolecular array bound to a substrate. As with all figures referenced herein, in which like parts are referenced by like numerals, FIG. 1 is not to scale, and certain dimensions may be exaggerated for clarity of presentation. The device 11 includes a plurality of reservoirs, i.e., at least two reservoirs, with a first reservoir indicated at 13 and a second reservoir indicated at 15. Each reservoir may be contained in, or disposed on, a substrate, such as well plate 111 (shown in FIG. 4A). Each is adapted to contain a fluid having a fluid surface. As shown, the first reservoir 13 contains a first fluid 14, and the second reservoir 15 contains a second fluid 16. Fluids 14 and 16 each have a fluid surface, respectively indicated at 17 and 19. Fluids 14 and 16 may be the same or different. As shown, the reservoirs are of substantially identical construction so as to be substantially acoustically indistinguishable, but identical construction is not a requirement. The reservoirs are shown as separate removable components but may, as discussed above, be fixed within a plate or other substrate. For example, the plurality of reservoirs may comprise individual wells in a well plate, optimally although not necessarily arranged in an array. Each of the reservoirs 13 and 15 is preferably axially symmetric as shown, having vertical walls 21 and 23 extending upward from circular reservoir bases 25 and 27 and terminating at openings 29 and 31, respectively, although other reservoir shapes may be used. The material and thickness of each reservoir base should be such that acoustic radiation may be transmitted therethrough and into the fluid contained within the reservoirs.

The device also includes an acoustic ejector 33 comprised of an acoustic radiation generator 35 for generating acoustic radiation and a focusing means 37 for focusing the acoustic radiation at a focal point within the fluid from which a droplet is to be ejected, near the fluid surface. The acoustic radiation generator 35 contains a transducer 36, e.g., a piezoelectric element, commonly shared by an analyzer. As shown, a combination unit 38 is provided that serves both as a controller and a component of an analyzer. Operating as a controller, the combination unit 38 provides the piezoelectric element 36 with electrical energy that is converted into mechanical and acoustic energy. Operating as a component of an analyzer, the combination unit receives and analyzes electrical signals from the transducer. The electrical signals are produced as a result of the absorption and conversion of mechanical and acoustic energy by the transducer.

As shown in FIG. 1, the focusing means 37 may comprise a single solid piece having a concave surface 39 for focusing acoustic radiation, but the focusing means may be constructed in other ways as discussed below. The acoustic ejector 33 is thus adapted to generate and focus acoustic radiation so as to eject a droplet of fluid from each of the fluid surfaces 17 and 19 when acoustically coupled to reservoirs 13 and 15, and thus to fluids 14 and 16, respectively. The acoustic radiation generator 35 and the focusing means 37 may function as a single unit controlled by a single controller, or they may be independently controlled, depending on the desired performance of the device. Typically, single ejector designs are preferred over multiple ejector designs because accuracy of droplet placement and consistency in droplet size and velocity are more easily achieved with a single ejector.

There are a number of ways to acoustically couple the ejector 33 to each individual reservoir and thus to the fluid therein. One such approach is through direct contact as is described, for example, in U.S. Pat. No. 4,308,547 to Lovelady et al., wherein a focusing means constructed from a hemispherical crystal having segmented electrodes is submerged in a liquid to be ejected. The aforementioned patent further discloses that the focusing means may be positioned at or below the surface of the liquid. However, this approach for acoustically coupling the focusing means to a fluid is undesirable when the ejector is used to eject different fluids in a plurality of containers or reservoirs, as repeated cleaning of the focusing means would be required in order to avoid cross-contamination. The cleaning process would necessarily lengthen the transition time between each droplet ejection event. In addition, in such a method, fluid would adhere to the ejector as it is removed from each container, wasting material that may be costly or rare.

Thus, a preferred approach would be to acoustically couple the ejector 33 to the reservoirs 13, 15 and reservoir fluids 14, 16 without contacting any portion of the ejector 33, e.g., the focusing means 37, with any of the fluids to be ejected. To this end, the present invention provides an ejector positioning means 43 for positioning the ejector 33 in controlled and repeatable acoustic coupling with each of the fluids 14, 16 in the reservoirs 13, 15 to eject droplets therefrom without submerging the ejector 33 therein. This typically involves direct or indirect contact between the ejector 33 and the external surface of each reservoir 13, 15. When direct contact is used in order to acoustically couple the ejector 33 to each reservoir 13, 15, it is preferred that the direct contact be wholly conformal to ensure efficient acoustic energy transfer. That is, the ejector 33 and the each of the reservoirs 13, 15 should have corresponding surfaces adapted for mating contact. Thus, if acoustic coupling is achieved between the ejector 33 and one of the reservoirs 13, 15 through the focusing means 37, it is desirable for the reservoir 13 or 15 to have an outside surface that corresponds to the surface profile of the focusing means 37. Without conformal contact, efficiency and accuracy of acoustic energy transfer may be compromised. In addition, since many focusing means have a curved surface, the direct contact approach may necessitate the use of reservoirs having a specially formed inverse surface.

Optimally, acoustic coupling is achieved between the ejector 33 and each of the reservoirs 13, 15 through indirect contact, as illustrated in FIG. 1A. In this figure, an acoustic coupling medium 41 is placed between the ejector 33 and the base 25 of reservoir 13, with the ejector 33 and reservoir 13 located at a predetermined distance from each other. The acoustic coupling medium 41 may be an acoustic coupling fluid, preferably an acoustically homogeneous material in conformal contact with both the acoustic focusing means 37 and each reservoir. In addition, it is important to ensure that the coupling medium 41 is substantially free of material having different acoustic properties than the coupling fluid medium itself. Furthermore, it is preferred that the acoustic coupling medium is comprised of a material having acoustic properties that facilitate the transmission of acoustic radiation without significant attenuation in acoustic intensity. Also, the acoustic impedance of the coupling medium 41 should facilitate the transfer of energy from the coupling medium 41 into the reservoir 13, and the coupling medium 41 should remain a liquid over the range of instrument operating temperatures. As shown, the first reservoir 13 is acoustically coupled to the acoustic focusing means 37, such that an acoustic wave is generated by the acoustic radiation generator 35 and directed by the focusing means 37 into the acoustic coupling medium 41, which then transmits the acoustic radiation into the reservoir 13.

In operation, reservoirs 13 and 15 are each filled with first and second fluids 14 and 16, respectively, as shown in FIG. 1. The acoustic ejector 33 is positionable by means of ejector positioning means 43, shown below reservoir 13, in order to achieve acoustic coupling between the ejector 33 and the reservoir 13 through acoustic coupling medium 41. Once the ejector 33, the reservoir 13, and the substrate 45 are in proper alignment, the acoustic radiation generator 35 is activated to produce acoustic radiation that is directed toward a free fluid surface 17 of the first reservoir 13. The acoustic radiation then travels in a generally upward direction toward the free fluid surface 17. The acoustic radiation is reflected under different circumstances. Typically, reflection occurs when there is a change in the acoustic property of the medium through which the acoustic radiation is transmitted. We have observed that a portion of the acoustic radiation traveling upward is reflected by the reservoir bases 25 and 27 as well as by the free surfaces 17 and 19 of the fluids contained in the reservoirs 13 and 15.

Thus, the present invention represents a significant improvement over known technologies relating to the acoustic assessment of the contents of reservoirs. As discussed above, acoustic assessment of the contents of liquid reservoirs typically involves placing a sensor in direct contact with the liquid. This means that the sensor must be cleaned between each use to avoid cross-contamination of the contents of the reservoirs. In contrast, the present invention allows for assessment of the contents of a plurality of containers without direct contact with the contents of the containers.

While other non-contact acoustic systems are known in the art, such systems provide only an indirect and approximate assessment of the contents of a reservoir. For example, the acoustic system described in U.S. Pat. No. 5,880,364 to Dam employs a technique in which the acoustic radiation is transmitted from a sensor through an air-containing portion of the container and then reflected from the air-liquid interface of the container back to the sensor. The roundtrip transit time is used to determine the volume of the air-containing portion of the container. The volume of liquid in the container is determined by subtracting the volume of the container not occupied by the liquid from the volume of the entire container. One drawback of this technique is that it cannot provide an accurate assessment of the liquid volume in a container when the volume of the container is not precisely known. This is particularly problematic when small reservoirs, such as those typically used in combinatorial techniques, are employed. The dimensional variability for such containers is relatively large when considered in view of the small volume of the reservoirs. Furthermore, the technique cannot be employed when the volume of the container is completely unknown or alterable. Finally, since acoustic radiation never penetrates the liquid, the reflected radiation can at best only provide information relating to the surface of the liquid, not information relating to the bulk of the liquid.

In contrast, because the invention involves the transmission of acoustic radiation through the portion of each reservoir adapted to contain a fluid, the transmitted acoustic radiation may provide information relating to the volume as well as the properties of the fluids in the reservoir. For example, the invention may provide a plurality of reservoirs, wherein a portion of each reservoir is adapted to contain fluid. A fluid contained in a reservoir must ordinarily contact a solid surface of the reservoir. When the invention is employed in a reflective mode, some of the generated acoustic radiation may be reflected by the interface between the fluid and the solid surface, while the remainder is transmitted through a fluid contained in the reservoir. The transmitted radiation is then reflected by another surface, e.g., a free surface, of the fluid contained in the reservoir. By determining the difference in roundtrip transit times between the two portions, the volume of the fluid in the reservoir may be accurately determined. In addition, transmission of acoustic radiation through the fluid allows characteristics of the acoustic radiation to be altered by the fluid. Thus, information relating to a property of the fluid may be deduced by analyzing a characteristic of the transmitted acoustic radiation.

In addition, air, like other gases, exhibits low acoustic impedance, and acoustic radiation tends to attenuate more in gaseous materials than in liquid or solid materials. For example, the attenuation at 1 MHz for air is approximately 10 dB/cm while that of water is 0.002 dB/cm. Since the acoustic system described in U.S. Pat. No. 5,880,364 to Dam requires acoustic radiation to travel through air, this system requires much more energy to operate. Thus, the present invention represents a more energy efficient technology, which may be employed to provide a more accurate and detailed assessment of the contents of a plurality of fluid reservoirs. Some of this additional accuracy can be achieved by using acoustic waves with higher frequencies (and hence shorter wavelengths), as these acoustic waves can be transmitted effectively through liquids yet would be very rapidly attenuated in air.

It will be appreciated by those of ordinary skill in the art that conventional or modified sonar techniques may be employed in the practice of this invention. Thus, acoustic (sonar) radiation is reflected back to the piezoelectric element 36, where the acoustic energy is converted into electrical energy for analysis. The analysis may be used, for example, to reveal whether the reservoir contains any fluid at all. If fluid is present in the reservoir, the location and the orientation of the free fluid surface within the reservoir may be determined, as well as the overall volume of the fluid. Characteristics of the reflected acoustic radiation may be analyzed in order to assess the spatial relationship between the acoustic radiation generator and the fluid surface, the spatial relationship between a solid surface of the reservoir and the fluid surface, as well as to determine a property of the fluid in each reservoir, e.g., viscosity, surface tension, temperature, acoustic impedance, acoustic attenuation, solid content, and impurity content. Once the analysis has been performed, a decision may be made as to whether and/or how to dispense fluid from the reservoir.

Depending on the type of assessment to be carried out, various techniques known in the art may be adapted for use in the present invention. Generally, interfacial energy measurements are routinely carried out using contact-angle measurement. The present invention may be adapted to perform such contact-angle measurements. In addition, a number of other acoustic assessment techniques are known in the art. For example, U.S. Pat. No. 4,391,129 to Trinh describes a system for monitoring the physical characteristics of fluids. The physical characteristics may be determined from acoustic assessment of the interfacial tension of fluids to a high degree of accuracy. U.S. Pat. No. 4,558,589 to Hemmes describes an ultrasonic blood-coagulation monitor. U.S. Pat. No. 5,056,357 to Dymling et al. describes acoustic methods for measuring properties in fluids through Doppler shifts. Other acoustic assessment techniques that may be adapted for use in the present invention are described, for example, in U.S. Pat. Nos. 4,901,245; 5,255,564; 5,410,518; 5,471,872; 5,533,402; 5,594,165; 5,623,095; 5,739,432; 5,767,407; 5,793,705; 5,804,698; 6,119,510; 6,227,040; and 6,298,726.

In order to form a biomolecular array on a substrate using the inventive device, substrate 45 is positioned above and in proximity to the first reservoir 13 such that one surface of the substrate, shown in FIG. 1 as underside surface 51, faces the reservoir and is substantially parallel to the surface 17 of the fluid 14 therein. Once the ejector, the reservoir, and the substrate are in proper alignment, the acoustic radiation generator 35 is activated to produce acoustic radiation that is directed by the focusing means 37 to a focal point 47 near the fluid surface 17 of the first reservoir. That is, an ejection acoustic wave having a focal point near the fluid surface is generated in order to eject at least one droplet of the fluid, wherein the optimum intensity and directionality of the ejection acoustic wave is determined using the aforementioned analysis, optionally in combination with additional data. The "optimum" intensity and directionality are generally selected to produce droplets of consistent size and velocity. For example, the desired intensity and directionality of the ejection acoustic wave may be determined by using the data from the above-described assessment relating to reservoir volume or fluid property data, as well as geometric data associated with the reservoir. In addition, the data may show the need to reposition the ejector so as to reposition the acoustic radiation generator with respect to the fluid surface, in order to ensure that the focal point of the ejection acoustic wave is near the fluid surface, where desired. For example, if analysis reveals that the acoustic radiation generator is positioned such that the ejection acoustic wave cannot be focused near the fluid surface, the acoustic radiation generator is repositioned using vertical, horizontal, and/or rotational movement to allow appropriate focusing of the ejection acoustic wave.

As a result, droplet 49 is ejected from the fluid surface 17 onto a designated site on the underside surface 51 of the substrate. The ejected droplet may be retained on the substrate surface by solidifying thereon after contact; in such an embodiment, it may be necessary to maintain the substrate at a low temperature, i.e., a temperature that results in droplet solidification after contact. Alternatively, or in addition, a molecular moiety within the droplet attaches to the substrate surface after contact, through adsorption, physical immobilization, or covalent binding.

Figure 1B:
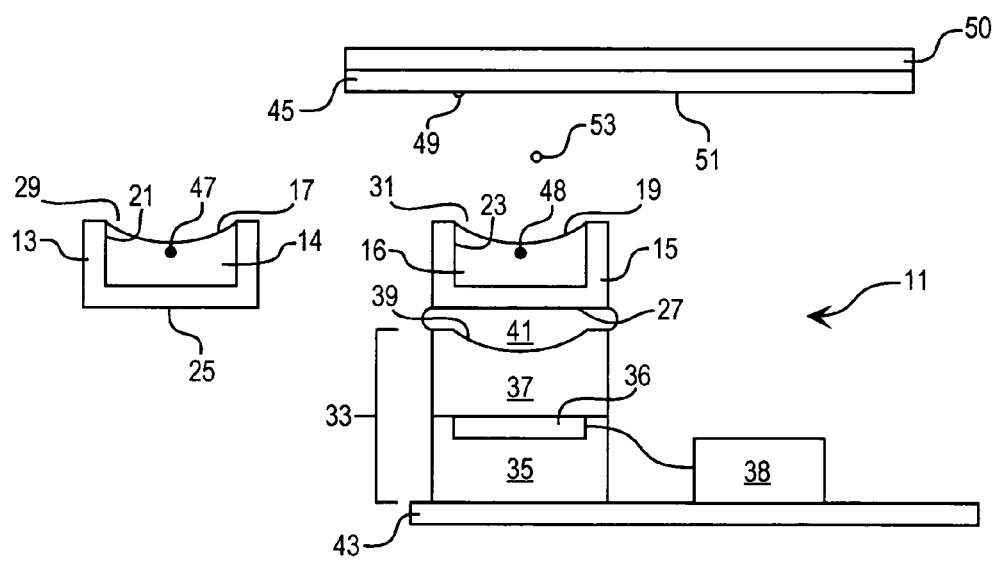

Then, as shown in FIG. 1B, a substrate positioning means 50 repositions the substrate 45 over reservoir 15 in order to receive a droplet therefrom at a second designated site. FIG. 1B also shows that the ejector 33 has been repositioned by the ejector positioning means 43 below reservoir 15 and is in an acoustically coupled relationship thereto by virtue of acoustic coupling medium 41. Once properly aligned, the acoustic radiation generator 35 of ejector 33 is activated to produce low energy acoustic radiation to assess the contents of the reservoir 15 and to determine whether and/or how to eject fluid from the reservoir. Historical droplet ejection data associated with the ejection sequence may be employed as well. Again, there may be a need to reposition the ejector so as to reposition the acoustic radiation generator with respect to the fluid surface, in order to ensure that the focal point of the ejection acoustic wave is near the fluid surface, where desired. Should the results of the assessment indicate that fluid may be dispensed from the reservoir, focusing means 37 is employed to direct higher energy acoustic radiation to a focal point 48 within fluid 16 near the fluid surface 19, thereby ejecting droplet 53 onto the substrate 45.

It will be appreciated that various components of the device may require individual control or synchronization to form an array on a substrate. For example, the ejector positioning means may be adapted to eject droplets from each reservoir in a predetermined sequence associated with an array to be prepared on a substrate surface. Similarly, the substrate positioning means for positioning the substrate surface with respect to the ejector may be adapted to position the substrate surface to receive droplets in a pattern or array thereon. Either or both positioning means, i.e., the ejector positioning means and the substrate positioning means, may be constructed from, for example, motors, levers, pulleys, gears, a combination thereof, or other electromechanical or mechanical means known to one of ordinary skill in the art. It is preferable to ensure that there is a correspondence between the movement of the substrate, the movement of the ejector, and the activation of the ejector to ensure proper array formation.

Accordingly, the invention relates to the assessment of the contents of a plurality of reservoirs as well as to dispensing a plurality of fluids from reservoirs, e.g., in order to form a pattern or an array, on the substrate surface 51. However, there are a number of different ways in which content assessment and fluid dispensing may relate to each other. That is, a number of different sequences may be employed for assessing the contents of the reservoirs and for dispensing fluids therefrom. In some instances, the contents of a plurality of reservoirs may be assessed before fluid is dispensed from any of the reservoirs. In other instances, the contents of each reservoir may be assessed immediately before fluid is dispensed therefrom. The sequence used typically depends on the particular fluid-dispensing technique employed as well as the intended purpose of the sequence.

Figure 2:
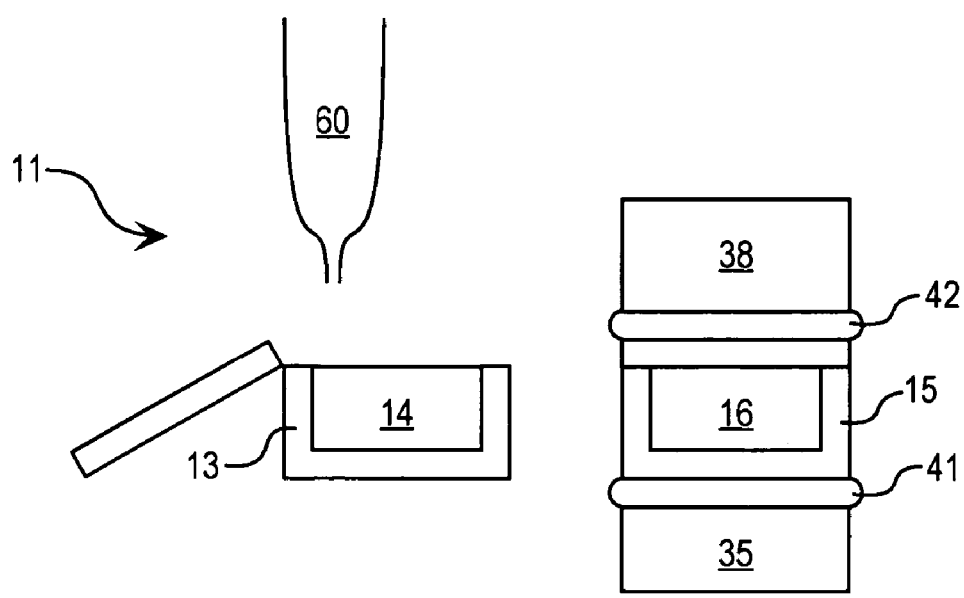
FIG. 2 schematically illustrates in simplified cross-sectional view an embodiment of the inventive device designed to permit acoustical assessment of the contents of a plurality of reservoirs in transmissive mode.

FIG. 2 illustrates an example of the inventive device that provides for assessment of the contents of a plurality of reservoirs in transmissive mode rather than in reflective mode. Considerations for the design and construction of this device are similar to those discussed above. Thus, the device 11 includes a first reservoir 13 and a second reservoir 15, each adapted to contain a fluid indicated at 14 and 16, respectively, and each of substantially identical construction. The first reservoir 13 is depicted in an open state, while the second reservoir is depicted in a sealed state. An acoustic radiation generator 35 is positioned below the reservoirs, and analyzer 38 is positioned in opposing relationship with the acoustic radiation generator 35 above the reservoirs.

In operation, the contents of each of the reservoirs are acoustically evaluated before pipette 60 is employed to dispense fluid therefrom. As shown, the contents 14 of the first reservoir 13 have already been acoustically assessed. As the assessment has revealed that the first reservoir 13 contains at least a minimum acceptable level of fluid 14, the first reservoir 13 is open and ready for fluid to be dispensed therefrom via pipette 60. The contents 16 of the second reservoir 15 are undergoing acoustic assessment, as depicted by FIG. 2, as the second reservoir 15 is interposed between the acoustic radiation generator 35 and the analyzer 38. The acoustic radiation generator 35 and the analyzer 38 are acoustically coupled to the second reservoir via coupling media 41 and 42, respectively. Once the acoustic radiation generator 35, the second reservoir 15, and the analyzer 38 are in proper alignment, the acoustic radiation generator 35 is activated to produce acoustic radiation that is transmitted through the reservoir 15 and its contents 16 toward the analyzer 38. The received acoustic radiation is analyzed by an analyzer 38, as described above.

The present invention can be used to determine the bulk temperature of materials. When the material between two interfaces is known and the distance the acoustic pulse travels in this material is also known, the speed of sound in the material can be determined by dividing the distance traveled by the travel time. The speed of sound in many materials changes monotonically with temperature, and hence knowledge of the speed of sound in the material is an indicator of the average temperature along the path of the acoustic wave within the material.

Thus the transit time for sound through a well plate bottom can be used as a thermometer for the microplate at a given well location. The speed of sound changes sufficiently as a function of temperature for most materials so that a temperature change of 1° C. can be detected with a 500 MHz signal, for a typical microplate thickness of about 500 µm. The resulting sensitivity is well in excess of that for the case discussed supra, in which the sampling time was required to be at least 100 times the transit time. For example, a 500 MHz signal has a sampling time of 2 ns. A typical transit time for 500 µm of polypropylene is about 710 ns. Therefore, the sampling time is about 355 times (710 ns/2 ns) the transit time. One can thus detect changes on the order of 1/355. For a material like polypropylene, with about a 0.3% change in the speed of sound per degree Celsius, one should obtain measurements accurate to within about 1° C.

Figure 3:
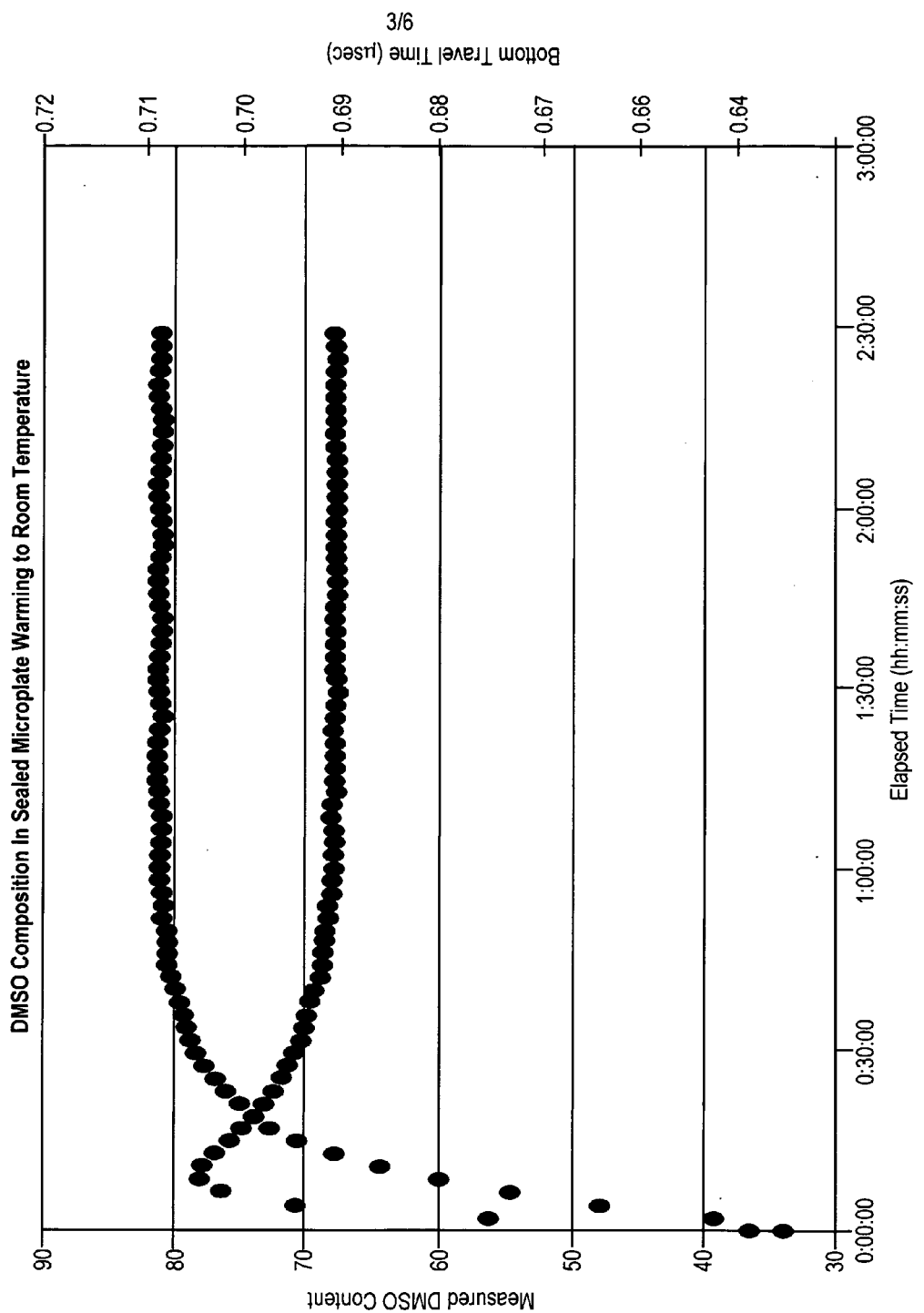
FIG. 3 is a chart showing measurements of apparent DMSO concentration in a sealed microplate as it was warmed to room temperature, calculated without correcting for the temperature.

FIG. 3 shows a graph for properties associated with a DMSO/water mixture in a sealed microplate that is warmed to room temperature. Elapsed time (hh:mm:ss) is shown along the x-axis. On the left-hand y-axis, the measured apparent DMSO content in a DMSO/water mixture is shown. On the right-hand y-axis, the well bottom travel time is shown in seconds. In the upper curve of FIG. 3, for example, the transit time of an acoustic wave through a polypropylene microplate (an average time for all 384 wells) is shown to increase for about an hour, settling at a value near 0.71 µsec.

The increase in travel time through the well plate bottom as it warms is due to the reduction in the speed of sound as a function of temperature for polypropylene. This response is typical for polypropylene materials. As discussed supra, Profax Polypropylene shows a 0.342% reduction in the speed of sound per ° C. (at temperatures close to room temperature). Thus, if a Profax Polypropylene plate experiences a 10% reduction in the speed of sound as it warmed to room temperature, an approximate 30° C. warming of the microplate bottom is indicated. In general, if the transit time can be measured through a plate that is made of a material for which the speed of sound is a known function of temperature, then the plate can act as a thermometer. The transit time gives a "bulk temperature" based on the average velocity of sound through the plate (e.g., well bottom). If the "bulk temperature" is representative of the fluid/plate interface temperature, then accurate values of impedance for the materials can be used to determine the reflected echo amplitude. From such data, a temperature-corrected/compensated impedance model, and thus reflection amplitude curve, can be constructed or empirically derived, as discussed supra.

FIG. 4 diagrammatically shows the principles associated with the use of the speed of sound as a parameter to determine the composition of a fluid in a well.

Figure 4A:
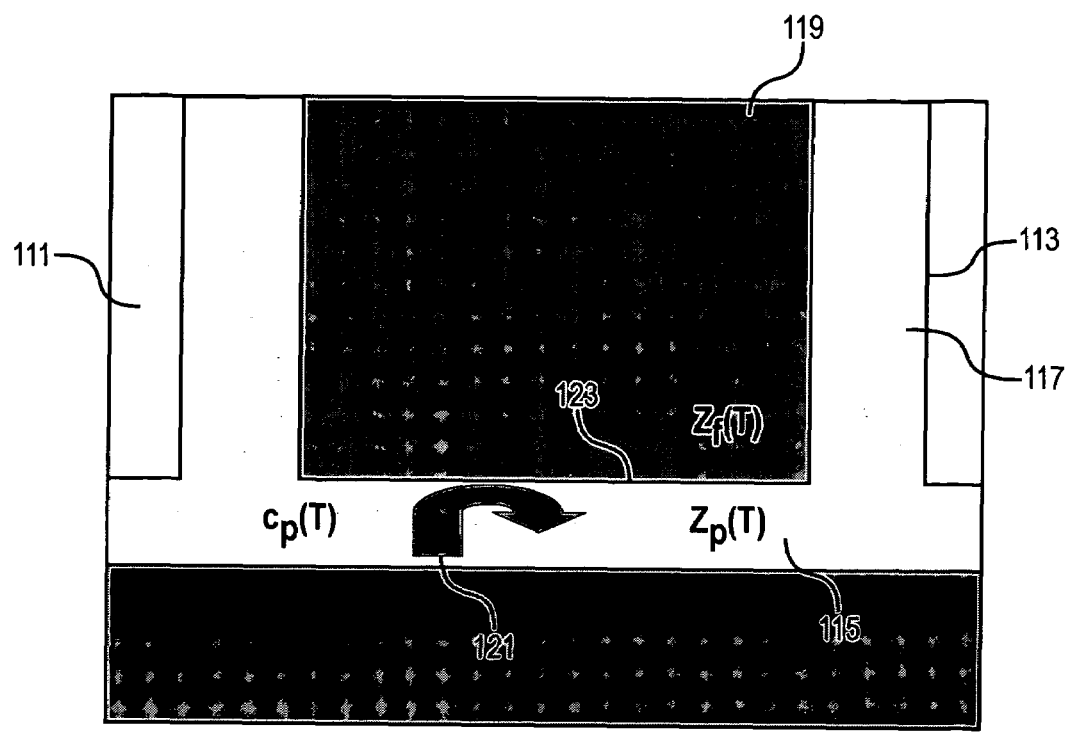
FIG. 4A-C schematically displays the use of the travel time of an acoustic wave in a well plate to determine temperature.

In FIG. 4A a well 113 in a well plate 114 has a base 115 and sidewalls 117. A fluid 119 is disposed in the well 113. An acoustic wave 121, generated by an acoustic wave generator 35, engages an interface 123 between the base 115 of the well 113 and the fluid 119 in the well 113. Because there is a substantial difference between the acoustic impedance Zf (T) of the fluid 119 and the acoustic impedance Zp (T) of the base 115, the acoustic wave 121 is reflected back to the analyzer provided in combination unit 38 for processing.

The travel time of the acoustic wave 121 inside the base 115 changes with temperature as the speed of sound inside the plate (cp) changes with temperature. Therefore, the bulk plate temperature can be calculated from the travel time, determined by a comparison of the time between the engagements of the acoustic wave with a lower surface 115a of the base 115 and the base/fluid interface 123. The arrival time at the transducer of the acoustic wave reflected from the two surfaces represents the time it takes for a round trip in the base.

Figure 4B:
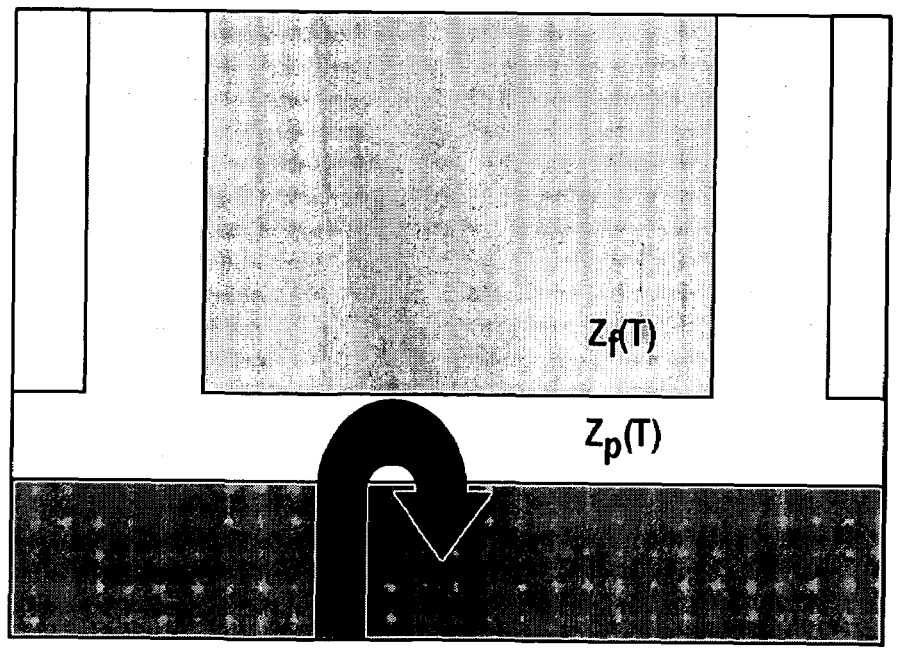

FIG. 4B shows that the acoustic impedance of the well fluid 119 and the well 113 change at different rates with changes in temperature. That is, as temperature rises, the impedance of fluid 119 in the well 113 may rise faster than the impedance of the well material because of the inherent difference in acoustic impedance between the fluid and the well material. This will change the amplitude of the reflected wave 121 at the base/fluid interface 123. This change could suggest a change in the DMSO composition of fluid that is, in fact, erroneous. Any model developed to use temperature to determine fluid composition would have to recognize and compensate for the phenomenon shown in FIG. 4B.

Figure 4C:
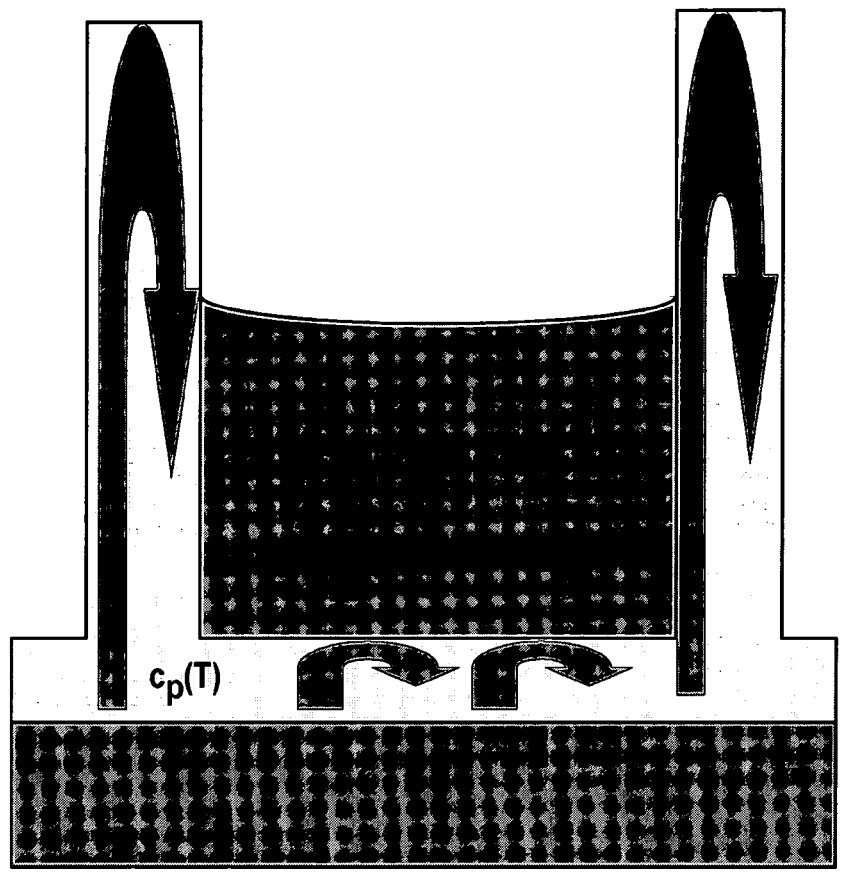
Figure 4D:
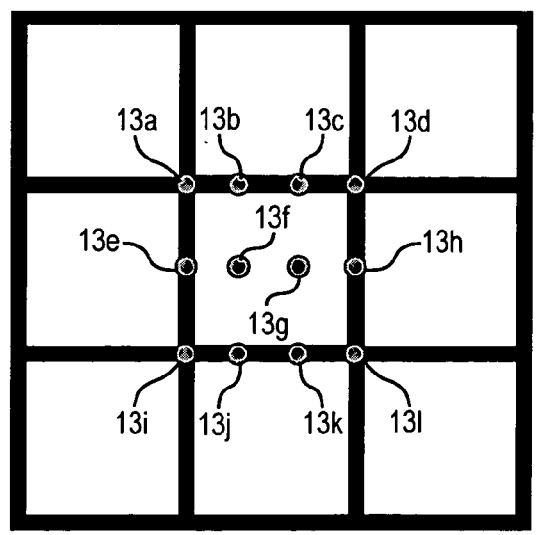
FIG. 4D is a top view of a well.

Because a single reading at the well base 115 may give an erroneous reading of temperature for the well 113 and the plate 111, it would be desirable to take multiple temperature readings in the plate 111 and the well 113. An example of this approach is shown in FIG. 4C. Bulk plate temperature can be determined at different locations in the plate 111 with respect to fluid 119. Multiple reflected transit times can be taken in the plate 111, the base 115 of the well 113, as well as the sidewalls 117. FIG. 4D, a top view of the well 113, shows test points 113a through 113l, used to obtain transit times employed for temperature measurements.

Figure 5:
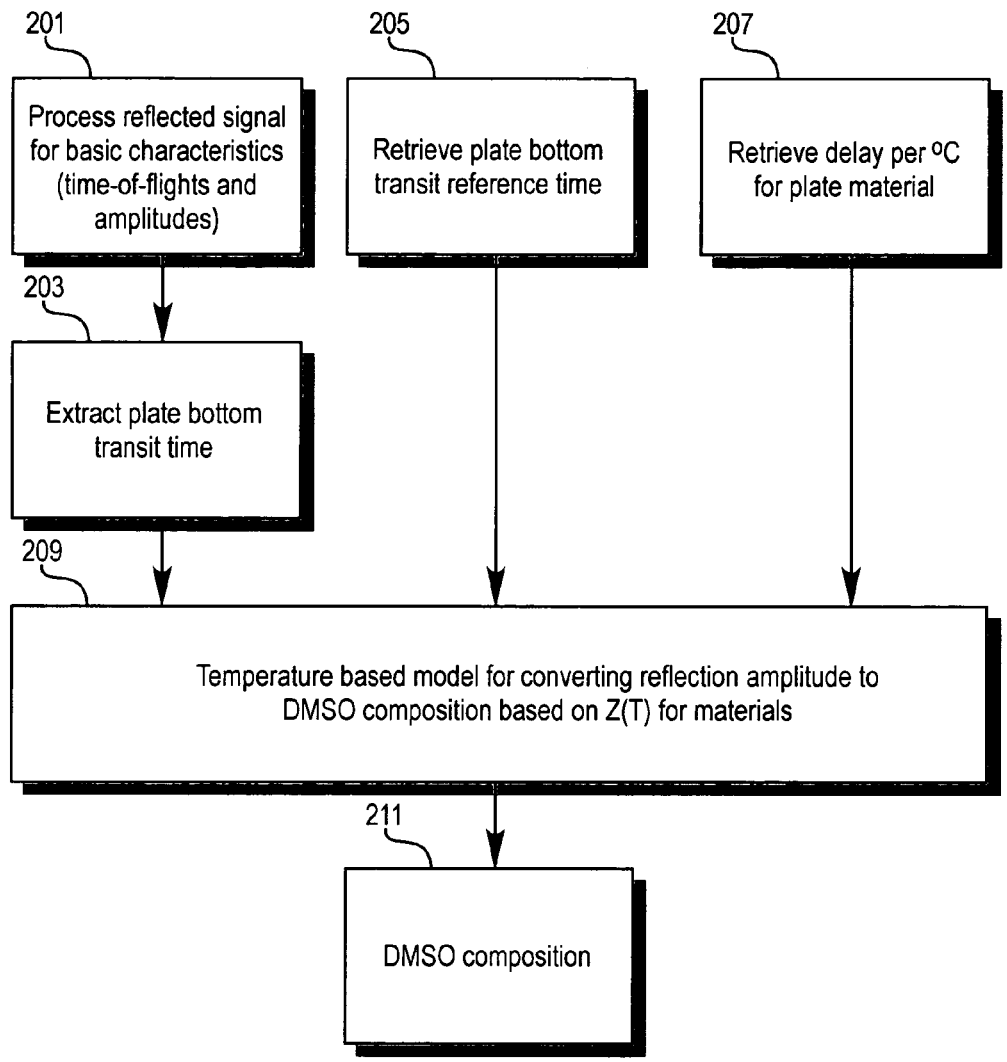
FIG. 5 displays a model for use in the analyzer to determine the acoustic impedance change with temperature for both the microplate and the fluid in the reservoir or well.

FIG. 5 provides a computer model for analyzing acoustic data to calculate DMSO content in a DMSO/water mixture with the use of temperature determination and correction. In step 201 the reflected signal is processed for time-of-flight and amplitude. From these data the plate bottom transit time is extracted (Step 203). In step 205 the plate bottom transit reference time is retrieved. In step 207, data are retrieved for the speed of sound as a function of temperature for the plate material. The data retrieved in steps 203, 205, and 207 are then delivered to a computer model 209, to convert reflection amplitude to DMSO content based on the acoustic impedance, Z(T), for the materials analyzed. The output of the model 209 is step 211, DMSO content.

Hence, the acoustic impedance change with temperature for both the microplate and well fluid (or solid if the temperature is below the freezing point of the liquid) would be corrected over a broad temperature range (−80° C. up to a "warm" room temperature).

Since pulse timing can be determined with great precision, by sampling or digitizing the echo return signal of the acoustic pulse, this method of "acoustic thermometry" can be implemented with the same electronics as is applied to other acoustic measurements for material characteristics.

Thicknesses for materials in reservoir containers vary with the material and reservoir used. Microplates used for optical assays typically have film bottoms of between 50 and 200 µm and may be composed of polystyrene or cyclic olefin copolymer. Microplates and tubes used for compound library storage have thicker bottoms, typically between 0.5 and 1.2 mm, and may be composed of polypropylene, cyclic olefin copolymer, or glass.

In general, the path of travel for the acoustic pulse directed within the walls of reservoirs will be larger that the travel distance within the bottom of a reservoir. Walls for standard microplates range from 2 mm to 12 mm in height, and so-called "deep wells" may possess walls with heights in excess of 25 mm. Storage tubes and mini tubes may range in size from 8 mm to over 25 mm. Since longer transit distances produce greater absolute differences in transit times as a function of temperature, it is easier to make accurate bulk temperature measurements in thicker portions of the reservoir.

The speed of sound as a function of temperature in materials can be determined by a variety of techniques known to those of skill in the art. For example, the speed of sound can be found empirically by immersing a sample of the material with a known thickness in a bath of controlled temperature, and then measuring the acoustic wave travel time through the material. Polymeric materials found in microplates show significant changes in sound speed as a function of temperature. For example, the speed of sound in some polypropylenes changes more than 0.3% per degree C. at temperatures near room temperature (22° C.). The speed of sound in polystyrenes changes about 0.1% per degree C. These values are approximate, since the wide range of molecular weight distributions and processing methods for these polymers influence the speed of sound. The speed of sound can vary with temperature by over 50% from these values, yet for a particular microplate, made with a particular polymer formulation and molding process, the speed of sound as a function of temperature is much more consistent at a given microplate well, and can serve as the basis for acoustic thermometry.

One temperature measurement of interest is that of the fluid in the reservoir, and the reservoir fluid may not be of either a known composition or a known depth. One object of the present invention is to determine the temperature of the fluid by inference from the temperature of the reservoir material around it. As shown in FIGS. 4A-4C, the speed of sound can be measured in both the reservoir bottom and the walls of the reservoir. These walls can be either the walls of a microtube or the separator walls of wells in a multi-well container such as a microplate. An average temperature along the path of the acoustic beam is collected by sending the beam into a given location. As discussed supra, to build a better spatial profile of the average temperature around a given reservoir fluid, acoustic pulses can be directed to multiple different locations, including some points located at the bottom of the fluid well and others within the reservoir wall.

It should be evident, then, that the invention provides a number of previously unrealized advantages for assessing the contents of a plurality of reservoirs. First, acoustic assessment is a generally noninvasive technique that may be carried out regardless of whether the reservoirs are sealed or open. That is, acoustic assessment does not require extracting a sample for analysis or require other mechanical contact that may result in sample cross-contamination. In addition, unlike optical detection techniques, optically translucent or transparent reservoirs are not required. This, of course, provides a wider range of choices for materials that may be employed for reservoir construction. In addition, the use of opaque material would be particularly advantageous in instances wherein the reservoirs are constructed to contain photosensitive fluids.

Thus, variations of the present invention will be apparent to those of ordinary skill in the art. For example, while FIG. 1 depicts the inventive device in operation to form a biomolecular array bound to a substrate, the device may be operated in a similar manner to format a plurality of fluids, e.g., to transfer fluids from odd-sized bulk containers to wells of a standardized well plate. Similarly, while FIG. 2 illustrates that the acoustic radiation generator and the detector are in vertical opposing relationship, other spatial and/or geometric arrangements may be employed so long as acoustic radiation generated is transmitted through at least a portion of the reservoir to the detector.

As another example, the invention may be employed to detect whether the contents of a sealed reservoir are at least partially frozen, without opening the reservoir. This would be useful when it is known that a reservoir contains a substance that is capable of existing as a fluid over a certain temperature range, but it is unclear as to the temperature history of the reservoir, e.g., whether freeze/thaw cycles existed. For example, water is capable of existing as a fluid at a temperature of about 0° C. to about 100° C. If it is unclear whether the exterior temperature of a reservoir is indicative of the reservoir's interior temperature, but the reservoir is known to contain liquid water, the inventive device is well suited to determine whether any or all of the contents of the reservoir is a fluid.

In addition, the invention may be constructed to be highly compatible with existing infrastructure of materials discovery and with existing automation systems for materials handling. For example, the invention may be adapted for use as an alternative or a supplement to content assessment means that are based on optical detection. In some instances, sonic markers may be provided in the reservoirs to identify the contents of the reservoir. Thus, the invention may be employed as a means for inventory identification and control in a number of contexts, including, but not limited, to biological, biochemical, and chemical discovery and analysis.

It is to be understood that while the invention has been described in conjunction with the preferred specific embodiments thereof, the foregoing description is intended to illustrate and not limit the scope of the invention. Other aspects, advantages, and modifications will be apparent to those skilled in the art to which the invention pertains.

All patents, patent applications, journal articles, and other references cited herein are incorporated by reference in their entireties.

We claim:

1. A method for acoustically determining a temperature-dependent property of a fluid in a reservoir, the reservoir being integral with or located on a substrate, the method comprising:
   (a) acoustically coupling an acoustic radiation generator and the reservoir, with the acoustic radiation generator located external to the reservoir;
   (b) activating the acoustic radiation generator to generate acoustic radiation and direct the acoustic radiation generated into and through the substrate toward the reservoir, such that the acoustic radiation is transmitted into the fluid in the reservoir and thereafter reflected from an interior surface of the reservoir;
   (c) measuring a temperature-dependent characteristic of the reflected acoustic radiation, said characteristic selected so as to correlate with the temperature of the fluid; and
   (d) employing the characteristic to determine the temperature-dependent property of the fluid in a temperature-compensated manner.

2. The method of claim 1, wherein the interior surface of the reservoir is an interface between the fluid and an interior surface of the reservoir.

3. The method of claim 2, wherein the temperature ($T_{F1}$) of the fluid is lower than 20° C. or greater than 25° C.

4. The method of claim 3, wherein the temperature-dependent characteristic of the reflected acoustic radiation is the acoustic velocity $V_{F1}$ in the fluid at temperature $T_{F1}$.

5. The method of claim 4, wherein (d) comprises comparing $V_{F1}$ with the acoustic velocity $V_{F\text{-}RT}$ of the fluid at a temperature $T_{RT}$ in the range of 20° C. to 25° C.

6. The method of claim 5, wherein (d) further comprises deriving from the difference between $V_{F1}$ and $V_{F\text{-}RT}$ the difference between the acoustic impedance $Z_{F1}$ of the fluid at temperature $T_{F1}$ and the acoustic impedance $Z_{F\text{-}RT}$ of the fluid at temperature $T_{RT}$.

7. The method of claim 6, wherein the temperature-dependent property is the composition of the fluid, and (d) further comprises determining the composition of the fluid in the reservoir from $Z_{F1}$ and $Z_{F\text{-}RT}$.

8. The method of claim 7, wherein the fluid in the reservoir is at least partially nonsolid.

9. The method of claim 7, wherein the fluid in the reservoir comprises at least one liquid.

10. The method of claim 9, wherein the fluid in the reservoir comprises a combination of miscible, partially miscible, or immiscible liquids.

11. The method of claim 10, wherein the fluid in the reservoir comprises a mixture of an organic solvent and an aqueous solvent.

12. The method of claim 11, wherein the fluid in the reservoir comprises a mixture of dimethylsulfoxide (DMSO) and water.

13. The method of claim 12, wherein the mixture contains more than 40 vol. % DMSO.

14. The method of claim 12, wherein the mixture contains more than 40 vol. % water.

15. The method of claim 1, wherein the reservoir is integral with a substrate.

16. The method of claim 15, wherein the reservoir is an individual container.

17. The method of claim 16, wherein the container is enclosed.

18. The method of claim 16, wherein the reservoir is a tube.

19. The method of claim 1, wherein the reservoir is one of a plurality of reservoirs, each reservoir being integral with or located on a substrate.

20. The method of claim 19, wherein the reservoirs are integral with a substrate.

21. The method of claim 20, wherein the substrate is a well plate and each reservoir is a well therein.

22. The method of claim 19, wherein steps (a) through (d) are repeated successively for additional reservoirs.

23. The method of claim 22, wherein steps (a) through (d) are repeated successively for each additional reservoir.

24. The method of claim 23, wherein steps (a) through (d) are repeated at a rate of at least 96 reservoirs per minute.

25. The method of claim 24, wherein steps (a) through (d) are repeated at a rate of at least about 384 reservoirs per minute.

26. The method of claim 25, wherein steps (a) through (d) are repeated at a rate of at least about 1536 reservoirs per minute.

27. The method of claim 26, wherein steps (a) through (d) are repeated at a rate of at least about 3456 reservoirs per minute.

28. The method of claim 27, wherein steps (a) through (d) are repeated at a rate of at least 10,000 reservoirs per minute.

29. The method of claim 1, wherein the acoustic radiation generated is directed into the reservoir through a region of the reservoir's exterior surface having an identifier thereon.

30. The method of claim 29, wherein the identifier is a barcode.

* * * * *